United States Patent [19]

Wolvek et al.

[11] 4,276,874
[45] Jul. 7, 1981

[54] ELONGATABLE BALLOON CATHETER

[75] Inventors: Sidney Wolvek, Brooklyn, N.Y.; Bruce L. Hanson, Wayne, N.J.

[73] Assignee: Datascope Corp., Paramus, N.J.

[21] Appl. No.: 960,789

[22] Filed: Nov. 15, 1978

[51] Int. Cl.³ .................... A61B 19/00; A61M 25/00
[52] U.S. Cl. ................................ 128/1 D; 128/349 B
[58] Field of Search ............... 128/1 D, 246, 325, 344, 128/349 B, 349 BV, 243, DIG. 9; 92/87; 285/97

[56] References Cited

U.S. PATENT DOCUMENTS

| 1,863,057 | 6/1932 | Innes | 128/243 |
|---|---|---|---|
| 2,460,473 | 2/1949 | Smith | 128/349 R |
| 2,548,602 | 4/1951 | Greenburg | 128/344 |
| 3,397,699 | 8/1968 | Kohl | 128/243 |
| 3,467,101 | 9/1969 | Fogarty et al. | 128/348 |
| 3,504,662 | 4/1970 | Jones | 128/1 D |
| 3,585,983 | 6/1971 | Kantrowitz | 128/1 |
| 3,692,018 | 9/1972 | Goetz et al. | 128/1 R |
| 3,720,200 | 3/1973 | Laird | 128/1 |
| 3,861,396 | 1/1975 | Vaillancourt et al. | 128/350 R |
| 3,895,637 | 7/1975 | Choy | 128/DIG. 9 |
| 3,896,815 | 7/1975 | Fettel et al. | 128/DIG. 9 |
| 3,938,529 | 2/1976 | Gibbons | 128/350 R |
| 3,939,820 | 2/1976 | Grayzel | 128/1 D |

FOREIGN PATENT DOCUMENTS

| 979,745 | 5/1951 | France | 128/344 |
|---|---|---|---|
| 512456 | 9/1939 | United Kingdom | 128/349 B |
| 1113484 | 5/1968 | United Kingdom | 128/349 B |

Primary Examiner—Robert W. Michell
Assistant Examiner—C. W. Shedd
Attorney, Agent, or Firm—Kenyon & Kenyon

[57] ABSTRACT

Inflatable and deflatable balloon catheters are disclosed. Catheters according to the invention have an expansion chamber that may be elongated to reduce its radial dimension without producing oblique or transverse folds or wrinkles. The inflatable chamber of the catheter is supported by an elongated support member of small diameter which has a continuously extending opening therein through which fluid is admitted to and withdrawn from the chanber. An axially movable elongating member is disposed within the expansion chamber for elongating the chamber. Axial movement of the elongating member elongates the chamber to decrease its radial dimension whereby feeding and guiding of the catheter is facilitated. In one embodiment, the support member is the gas supply tube extending into the chamber and the continuously extending opening is a helical slit running along at least part of the tube enclosed by the chamber. In another embodiment, the support member is a helical spring secured within the chamber to one end of the gas supply tube and the continuously extending opening is the space between coils of the spring. Also, in the disclosed embodiments, the catheter is an intra-aortic balloon catheter. A method is also disclosed for fabricating and using catheters according to the invention.

18 Claims, 14 Drawing Figures

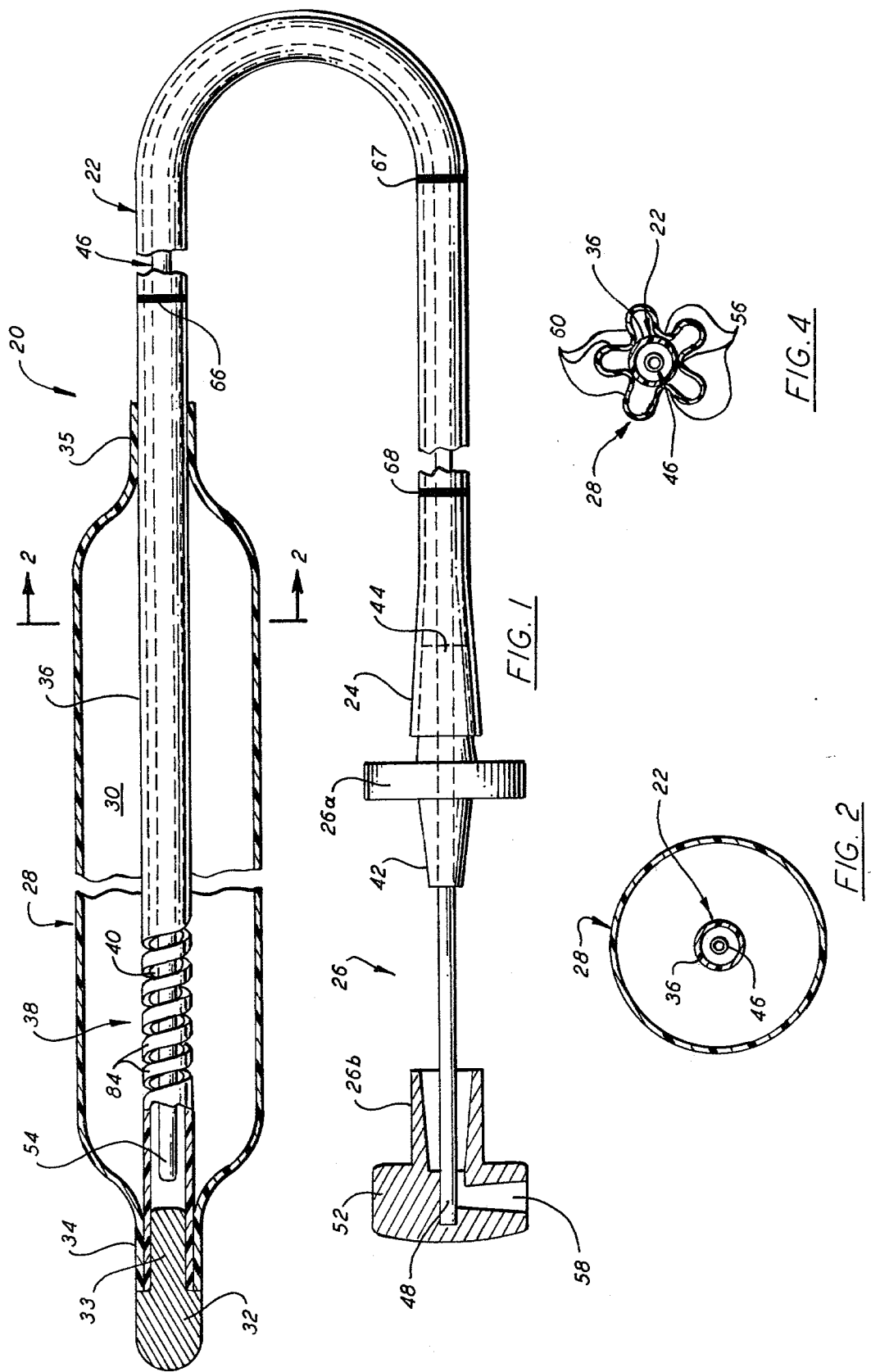

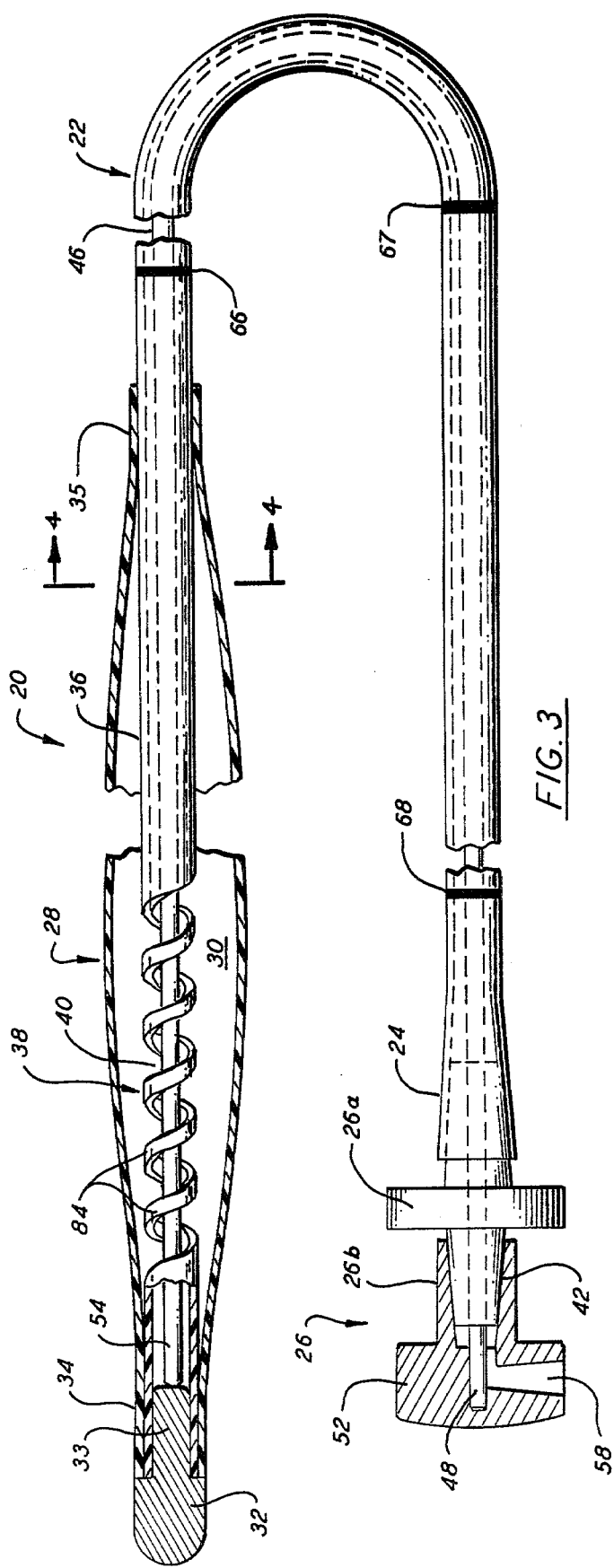
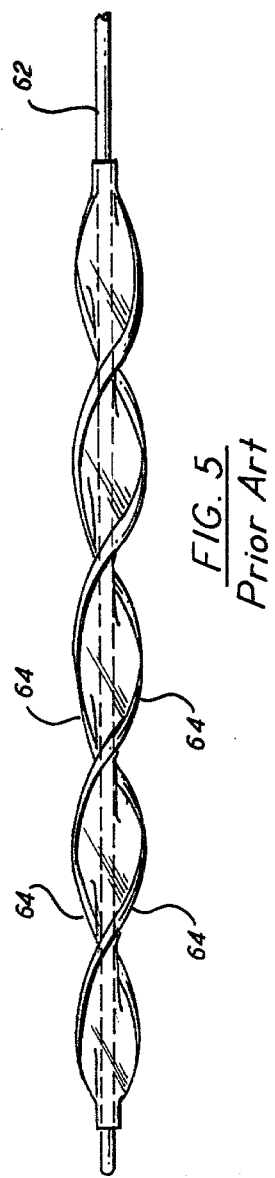
FIG. 3
FIG. 5
Prior Art

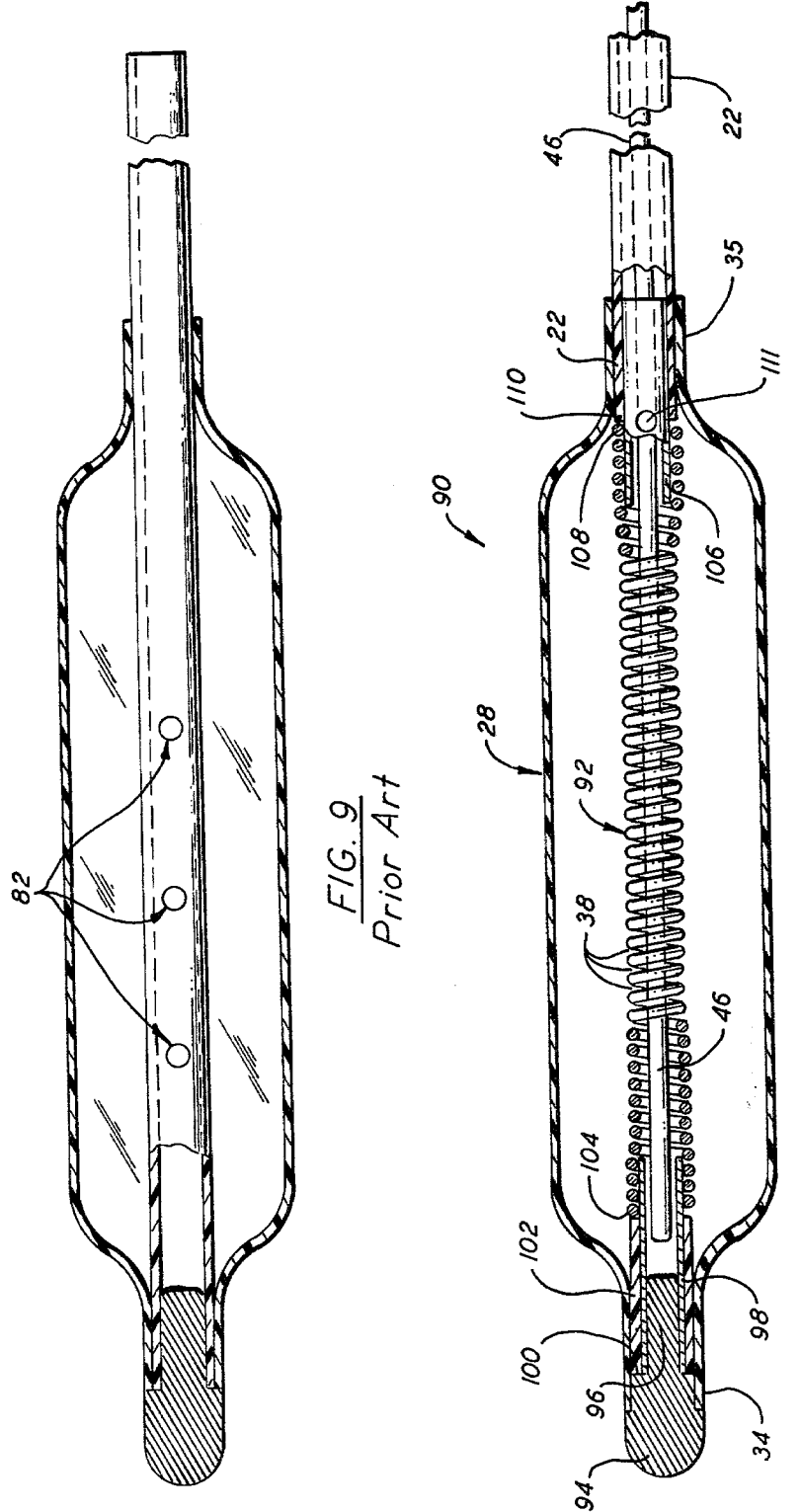

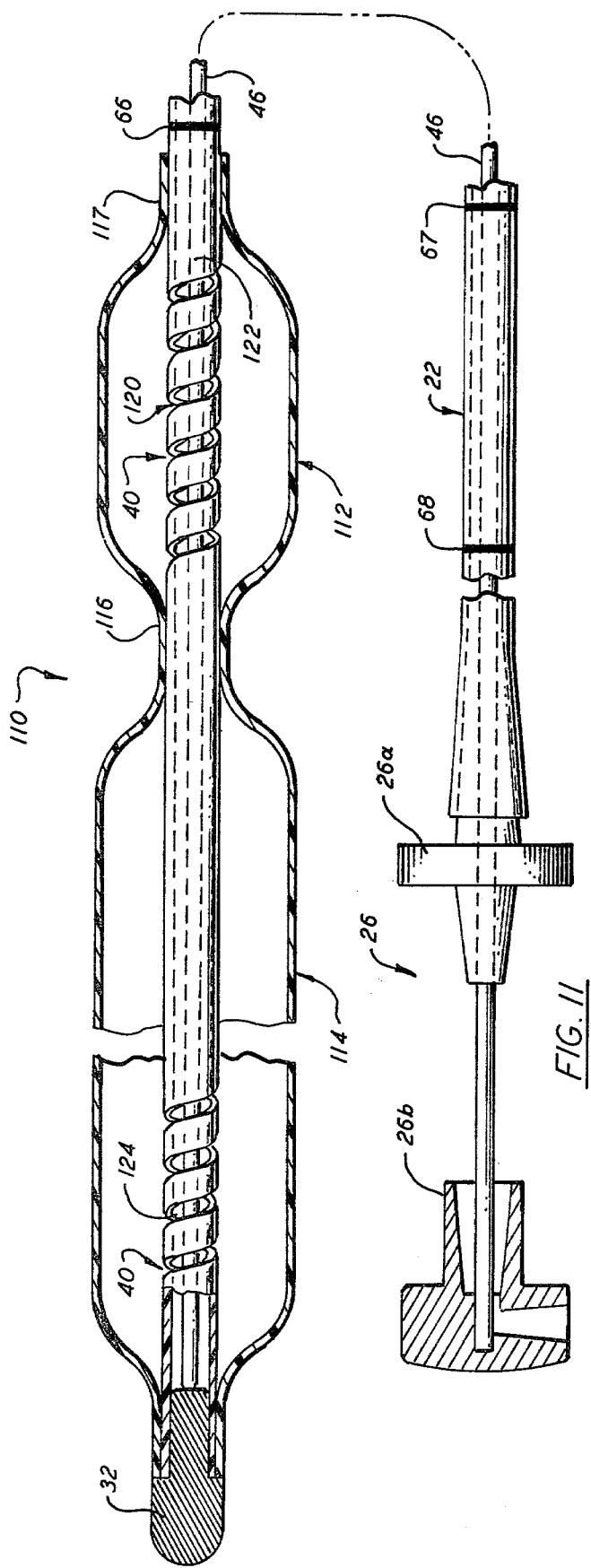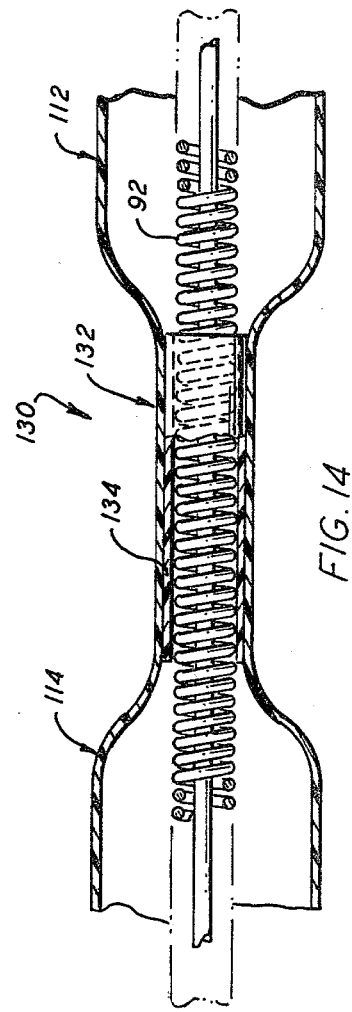
FIG. 11
FIG. 14

ELONGATABLE BALLOON CATHETER

The present invention relates to catheters and more particularly to an inflatable balloon catheter, particularly for use in intra-aortic pumping.

Intra-aortic balloon pumping is a recognized method of cardiac assistance for a failing heart. It is also a recognized method of treating cardiogenic shock and has been used to help wean a patient away from cardiopulmonary bypass, to support a patient during a difficult postoperative period, and to provide a pulsatile flow to the linear flow supplied by the cardiopulmonary bypass device. Intra-aortic balloon pumping has also been used therapeutically after myocardial infarction to limit the extension of necrosis and has been used as a therapy for angina pectoris.

Catheters for intra-aortic balloon pumping presently utilize a nonstressed or nondistensible balloon, i.e., the balloon is not stretched during inflation and deflation and substantially never changes its surface area, inflating and deflating with a predetermined volume of appropriate fluid to achieve phasic operation; the balloon surface area is always substantially equal to that of a fully inflated balloon. The intra-aortic balloon catheters of the prior art are relatively stiff and bulky and have a large "entering" cross-section. The femoral artery has heretofore been used for insertion of these stiff and bulky intra-aortic balloon catheters because of the large diameter of that artery. However, considerable surgery must be performed in order to reach and isolate the femoral artery. In addition, a large incision must be made in the femoral artery wall to permit introduction of these prior art devices. The safeness of intra-aortic balloon pumping using the catheters of the prior art has been questioned since they can cause and in some instances have caused aortic dissections, perforations and trauma mainly because of the relative stiffness of the devices. Additionally, this stiffness prevents precise maneuverability of the catheter within the vascular structure and thereby limits its potential for efficacy.

It is recognized in the prior art that insertion and guiding of catheters is difficult and that trauma and damage to the incision and blood vessel may occur during said insertion and guiding. In some prior art catheters, in order to permit insertion and guiding of the catheter in a blood vessel, the balloon is rolled or spirally wrapped around its underlying catheter tube. See, for example, FIGS. 3 and 4 of Goetz et al. U.S. Pat. No. 3,692,018. While this makes the catheter more compact, it is not entirely satisfactory because folds resulting from the rolling or wrapping of the balloon are arranged obliquely or transversely with respect to the lining of the blood vessel. Such folds, being transverse to the incision and intimal lining, may cause the trauma and damage mentioned above. This is particularly true for catheters inserted into arteries which have a highly vulnerable and easily damaged lining (tunica intima). In Graysel, U.S. Pat. No. 3,939,820, the size of the catheter can be reduced by replacing the catheter tube within the balloon by a wire. However, the balloon is nonetheless spirally wrapped around the wire and the transverse folds or wrinkles remain. Additionally, the wire in Grayzel is relatively inflexible in order to adequately support the balloon.

Intra-aortic balloon catheters should rapidly and non-turbulently inflate and deflate for good pumping operation. However, the inflating and deflating action of prior art catheters is not entirely satisfactory.

In accordance with the present invention, new and improved catheters are provided.

It is an object of the present invention to provide a new and improved catheter.

It is another object of the present invention to provide a catheter which may be inserted through small incisions or even by percutaneous insertion.

It is also an object of the present invention to provide a catheter which may be inserted into small blood vessels.

It is another object of the present invention to provide a catheter that will not subject the incision or the interior of a blood vessel, or body canal or passage, to injury by the oblique wrinkles of a "wrapped" profile.

It is another object of the present invention to provide a catheter that is rapidly and non-turbulently inflatable and deflatable.

It is another object of the present invention to provide a catheter capable of being configured to have a cross-sectional diameter approximately that of the inflating gas supply tube of the catheter.

It is another object of the present invention to provide a catheter that can be maneuvered and positioned in a blood vessel, canal or passage, and that can be repositioned therein without a removable stiffening member in the catheter.

It is also an object of the present invention to provide a catheter having a distal portion which may be "flow-directed."

It is an object of the present invention to provide single and multi-chambered balloon catheters embodying the aforementioned objects.

These and other objects are achieved by catheters of the present invention. Catheters according to the present invention include an expansion chamber and means for elongating the expansion chamber to reduce its radial dimension without producing oblique or transverse folds or wrinkles. According to one aspect of the invention, the catheters include means in the form of a continuously extending opening in the interior of the expansion chamber for admitting and withdrawing fluid for inflating and deflating the chamber.

In accordance with disclosed embodiments of the invention, the means for elongating the expansion chamber include elongatable supporting means within the chamber and an actuable member disposed within the chamber for elongating the supporting means upon actuation of the member. In the disclosed embodiments, the expansion chamber may resume its original dimensions upon deactuation of the actuable member. The catheter is maneuverable and may be positioned and repositioned within a blood vessel, canal or passage with the actuable member removed. Preferably, the supporting means has a cross sectional diameter not larger than approximately the diameter of a catheter tube for supplying fluid to the chamber.

Further in accordance with disclosed embodiments, the catheters comprise a hollow fluid supply or catheter tube, an expansion chamber secured to or enclosing at least part of the tube, a continuously extending opening communicating the interior of the tube to the interior of the chamber, and a tip member at the distal end of the catheter, distal being referenced with respect to the free end of the catheter adjacent the expansion chamber. The actuable member comprises an elongated member, preferably a rod-like member, movably disposed in the tube between the tip and a fitting. Axial movement of the actuable member against the tip actuated by movement of the fitting elongates the chamber to decrease its radial dimension.

The continuously extending opening has an area substantially at least equal to the radial cross-section of the fluid supply tube, and in one embodiment, the continuously extending opening is a helical slit running along at least part of the tube enclosed by the chamber. In another embodiment, a helical spring within the chamber is secured to the tube and the continuously extending opening is the space between coils of the spring.

The elongatable support means provide an extremely flexible catheter while at the same time maintaining sufficient longitudinal and torsional support of the expansion chamber to permit manuevering, positioning and repositioning even after the actuable member has been withdrawn. Upon deactuation or withdrawal of the actuable member, the chamber and support means assume their non-elongated, axially shortened configuration. Thus, the elongatable support means exhibits the spring-like qualities of memory, flexibility and longitudinal support.

The continuously extending opening preferably has an area substantially greater than the cross-sectional area of the fluid supply tube. Catheters according to the invention may therefore be smaller in cross section than prior art catheters while providing an increased and non-turbulent fluid flow to and from the expansion chamber. The continuously extending opening and the means for elongating the expansion chamber and its encompassed catheter tube provide, according to the invention, an inordinately large area of communication through the tube to the expansion chamber for the inflating and deflating fluid without reducing the ability of the tube to support the chamber.

The invention also includes a method for fabricating catheters according to the invention having an inflatable chamber and support means therefor including an axially elongatable portion, the method comprising forming a fluid-tight seal between the distal end of the chamber and the support means, axially elongating the support means, and forming a fluid-tight seal between the proximal end of the chamber and the support means while the support means is axially elongated.

Catheters according to the invention are insertible through smaller incisions and body openings and may be guided into and through smaller and more tortuous canals and passages, and blood vessels in particular. The catheters do not possess the transverse folds of the prior art devices and are flexible, maneuverable and easily guided within the blood vessel, canal or passage. They are also quickly and non-turbulently inflatable and deflatable. For intra-aortic balloon pumping, the catheters of the inention are insertible in a small incision in blood vessels other than the femoral artery.

In the preferred embodiments, the chamber is formed by an elastomeric balloon and the catheter is an intra-aortic balloon catheter. According to the present invention, the balloon or chamber is stretched axially or longitudinally when inserted so that its circumference collapses about the contained catheter tube in a series of longitudinal folds of the balloon. Thus, the cross-sectional diameter of the collapsed balloon portion is approximately that of the underlying catheter tube. The axial or longitudinal folds slide easily into the incision and along the vessel lining since the direction of the folds is always parallel to the axis of the arteriotomy and of the blood vessel. At no time is the lining of the artery faced with the obliquely facing and advancing folds as in the prior art. Elongating the balloon allows it to conform very closely to the underlying catheter tube, obviates the need to wrap the balloon around the underlying catheter tube and permits an easier and less traumatic entry of the catheter into a small opening. The elongating means according to the invention is flexible and, in addition to ease of entry, allows effective directional conrol, i.e., maneuverability, by either flow direction or by teaching wire manipulation. The extreme flexibility and controllability of catheters according to the invention, combined with the ease of insertion, makes it possible to insert the catheter into smaller and more accessible arteries than the femoral artery, for example the brachial or the axillary artery. Intra-aortic balloon pumping can be carried out with catheters according to the invention without undergoing the extensive surgery of a femoral arteriotomy and therefore may become available to many more patients. Those patients for whom the standard transfemoral approach is impossible becaue of atheromatous femoral arteries, obstructive aortoiliac disease, or a contaminated or previously cannulated groin may now be treated by the more easily inserted and more flexible catheters of the invention.

It is therefore contemplated that the catheters of the invention inserted according to the invention will make intra-aortic balloon pumping available to many more people than can now be treated by the use of the relatively stiff, bulky prior art balloon catheters and the obligatory use of the femoral arteries because of the large "entering" bulk of the prior art catheters.

It is also within the contemplation of the present invention that catheters according to the invention be percutaneously insertable, i.e., insertable through the skin without surgery.

These and other aspects of the invention will be more apparent from the following description of the preferred embodiments thereof when considered with the accompanying drawings and appended claims.

The present invention is illustrated by way of example and not limitation in the figures of the accompanying drawings in which like reference indicate similar parts and in which:

FIG. 1 is a longitudinal section view of the catheter according to the invention showing the rod for elongating the balloon and the continuously extending opening in the form of a helical slit located towards the distal end of the balloon for admitting and removing fluid to and from the balloon, the balloon being shown in its non-elongated configuration and the rod in its non-extended position;

FIG. 2 is a section view taken along lines 2—2 of FIG. 1;

FIG. 3 is a longitudinal section view of the catheter of FIG. 1 in which the rod is axially extended in the balloon and the balloon is in its elongated configuration;

FIG. 4 is a section view taken along line 4—4 of FIG. 3;

FIG. 5 is a longitudinal section view of part of a prior art catheter showing the balloon spirally wrapped about the catheter tube for insertion into the femoral artery;

FIG. 9 is a longitudinal section view of part of a prior art catheter showing the balloon and discrete openings for admitting and removing fluid to and from the balloon;

FIG. 10 is a longitudinal section view of part of a catheter according to yet another embodiment of the invention showing the balloon, the rod for elongating the balloon and the continuously extending opening in the form of a spiral space between coils of a coil spring in which the rod is disposed, the ballon being shown in its non-elongated configuration and the rod in its non-extended position;

Figure 12:
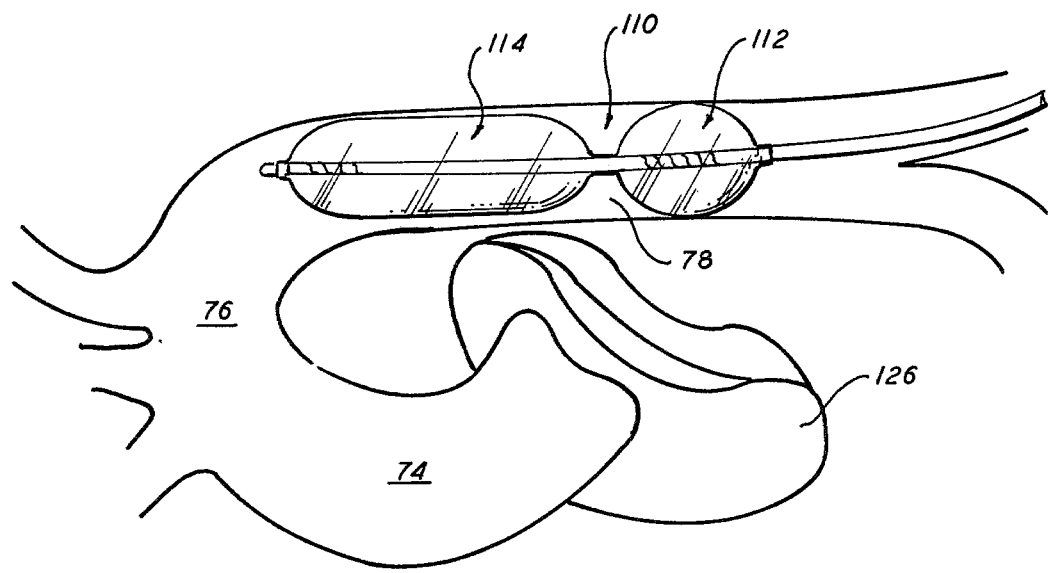
Figure 13:
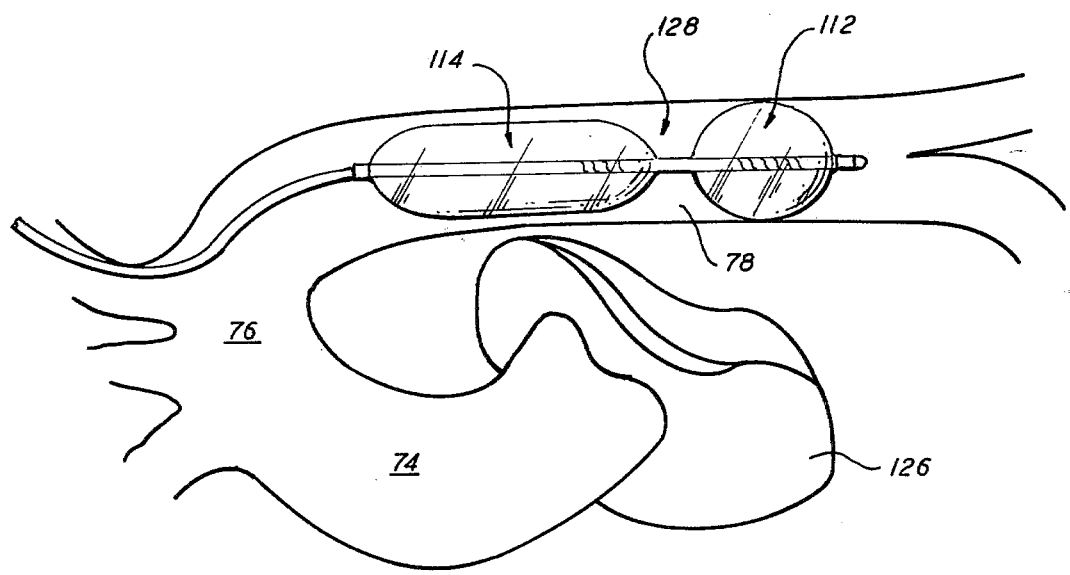

FIG. 11 is a longitudinal section view of a dual-chambered catheter according to another embodiment of the invention showing a distal pumping balloon, a proximal occluding balloon, the rod for elongating the balloons, and continuously extending openings in the form of helical slits for admitting and withdrawing fluid to and from the balloons, the balloons being shown in their non-elongated configurations and the rod in its non-extended position;

FIG. 12 is a diagramatic illustration showing the catheter of FIG. 11 in the aorta;

FIG. 13 is a diagramatic illustration showing a dual-chambered catheter according to another embodiment of the invention in the aorta, the catheter being similar to that of FIG. 11 with the occluding ballon distally disposed and the pumping balloon proximally disposed; and FIG. 14 is a longitudinally section view of part of a dual chambered catheter according to still another embodiment of the invention showing the neck portion of a distal pumping balloon and a proximal occluding balloon similar to the catheter of FIG. 11 in which the continuously extending opening is provided by the spiral space between the coils of a coil spring as in FIG. 11.

As shown in FIG. 1, catheter 20 according to the invention includes a hollow, flexible catheter (gas supply) tube 22 affixed at one end 24 thereof to a connector such as a luer 26 and adjacent the other end thereof to an elastomeric balloon 28. Catheter 20 is an omnidirectional intra-aortic balloon catheter and includes the single balloon chamber 30. In accordance with the preferred embodiments illustrating the invention and not by way of limitation, the balloon is not stressed or stretched during inflation and deflation, i.e., the balloon is non-distensible and has substantially the same surface area when inflated (FIGS. 1 and 2) and when deflated (FIGS. 3 and 4). The catheter terminates at its distal end in a rigid tip 32 fluid-tightly affixed in the distal end 34 of the balloon. The tip 32 has a reduced diameter portion 33 which the distal end of the tube 22 encloses and to which the tip is fluid-tightly affixed. The elastomeric balloon 28 is affixed at opposed ends 34, 35 thereof to and encloses a section 36 of tube 22. The tube 22 is formed of a flexible, biologically acceptable material such as, for example, polyurethane. The luer 26 is also formed of a biologically acceptable material such as, for example, polyethylene or polypropylene. The tip 32 is formed from, for example, stainless steel or Lexan. As shown, tip portion 33 and male luer 26a are inserted into the interior of tube 22 with the tip 32 and luer 26a being secured to the tube 22 in a fluid-tight manner by means such as, for example, adhesives, heat sealing, welding, windings etc. The tip, tube and male luer are thereby co-extensive at least in part to form a continuous member having good flexibility at the tip/tube and luer/tube regions with the diameter of the tube within the balloon supporting it having a cross-sectional diameter approximately equal to that of tube 22. Balloon 28 is made of a biologically acceptable elastomeric material, such as for example, a thin film of polyurethane and is affixed at ends 34, 35 to tube 22 in a fluid-tight manner by means such as those mentioned above for affixing the tip and male luer to the tube.

A continuously extending opening 38 communicating with the interior of tube 22 is disposed in section 36 thereof proximate balloon end 34 for admitting fluid, usually a gas, into and withdrawing fluid from the interior of the balloon to inflate and deflate it. As shown in FIG. 1, the continuously extending opening is a helical slit 40 running along part of tube section 36. Male luer 26a includes fluid port 42 and has passage 44 therethrough communicating with the interior of balloon 28 through opening 38 and the interior of tube 22. Thus, fluid may be supplied to and withdrawn from the interior of balloon 28 to inflate and deflate it through port 42. Gas, such as carbon dioxide and helium, or liquids are used to inflate balloon 28 when the catheter is used for intra-aortic balloon pumping.

Slidably disposed within the interior of hollow tube 22 is an elongated member 46 which extends from proximate tip 32 to and through male luer 26a. Member 46 is in the form of a relatively stiff rod and is made of a material such as, for example, stainless steel. The diameter of member or rod 46 is substantially less than the inside diameter of tube 22 so that the rod is freely axially movable in the tube. The stiffness of the rod and its diameter insure that the rod will be fully movable along the length of the tube and will not become entrapped therein. The helical slit permits passage of fluid therethrough while preventing the rod from protruding from the catheter tube and possibly damaging or puncturing the balloon.

The length of rod 46 is greater than the length of tube 22, and end 48 of rod 46 is permanently secured in female luer 26b by means such as adhesives. Female luer 26b has its end 52 shaped in the form of a handle or knob which is adapted to be grasped to slide the female luer towards and seat it on male luer 26a as shown in FIG. 3. Movement of the female luer to the right (FIG. 3) causes rod 46 to move to the left until its distal end 54 abuts portion 33 of tip 32. Continued movement to the left of rod 46 causes balloon 28 to stretch axially or longitudinally, and opening 38 to widen until female luer 26b is engaged by and seated on male luer 26a, the balloon then assuming the configuration shown in FIGS. 3 and 4. This axial elongation of the balloon substantially reduces its radial dimension from that shown in FIG. 2, to that shown in FIG. 3. The elongated configuration of the balloon is generally elliptical in longitudinal section, having as a major axis (FIG. 3) its cross-sectional axial diameter. Thus, movement of rod 46 to the left increases the major axis of the balloon until the minor axis thereof (FIG. 4) has been reduced to an extent which causes the balloon to collapse on the enclosed tube section 36. Since the balloon is non-distensible and thus always retains its specific circumferential girth, it collapses along lines 56 (FIG. 4) arranged about the circumference of the tube section and running axially or longitudinally along the balloon between its ends 34, 35. The balloon is thus longitudinally folded. Elongation of the catheter 20 is confined to the balloon and the tubular section enclosed by it since the balloon is secured at its ends to the underlying catheter tube. The collapsing of the balloon is enhanced by the air vent passage 58 in female luer 26b which allows the escape of air trapped within the balloon as its volume is reduced during elongation. Venting reduces the height of the longitudinal folds 60. The collapse of the elongated balloon upon tube section 36 may be further enhanced by applying a vacuum to the vent passage 58 of female luer 26b while it is engaged with male luer 26a during balloon elongation. This is accomplished by fitting one end of a suction line having a male luer connector to the vent passage 58 which has a female luer connector. Air trapped within the balloon is evacuated by a suction source via the vent passage.

Thus, as shown in FIG. 3, the catheter according to the invention presents an extremely small and streamlined entering profile. The longitudinal folds 60 are small in height and taper between balloon ends 34 and 35, running in the direction of the line of entry into a blood vessel. Because of the presence of the air vent, the longitudinal folds are shallow and compliant, and are conformable to the size and shape of the incision. At no time during the balloon insertion do the shallow, compliant folds present an oblique edge to the incision or to the lining of the blood vessels.

Since, as mentioned, balloons are generally not distended during intra-aortic balloon pumping and always have a surface area equal to the fully inflated balloon, the balloons of prior art catheters were wrapped about the catheter tube 62 as shown in FIG. 5 to reduce the catheter profile for insertion into a blood vessel. However, the entering profile of such prior art catheters is bulky and presents a series of oblique or transverse folds 64 to the incision and to the lining of the blood vessels. The balloon is not "unwrapped" after insertion into the entering vessel but is advanced in its wrapped configuration. Injury may be caused to the blood vessel linings from the oblique folds 64 for a considerable distance. The aforementioned Grayzel patent reduces the entering size of the catheter by replacing the enclosed tube with a wire. However, the balloon is nonetheless wrapped as shown in FIG. 5 herein and the series of oblique folds 64 are still presented to the incision and to the arterial lining. In addition, replacement of the tube 62 by a wire requires a comparatively stiff wire which makes it difficult to force the catheter to follow and conform to the tortuous, curved pathway of the vascular system. Such forcing may result in considerable scraping and damage to the arterial lining.

Figure 6:
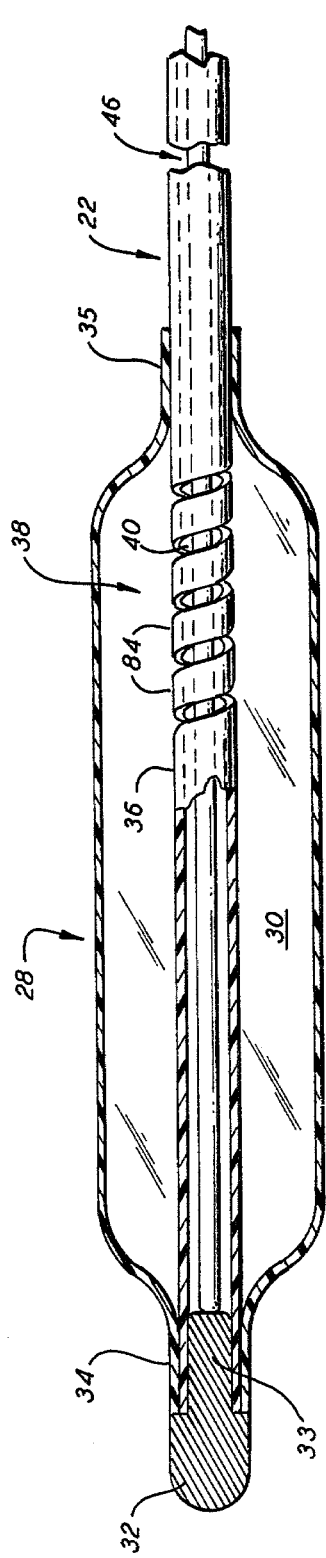
FIG. 6 is a longitudinal section view similar to that of FIG. 1 showing part of a catheter according to another embodiment of the invention in which the continuously extending opening is located towards the proximal end of the balloon.
Figure 7:
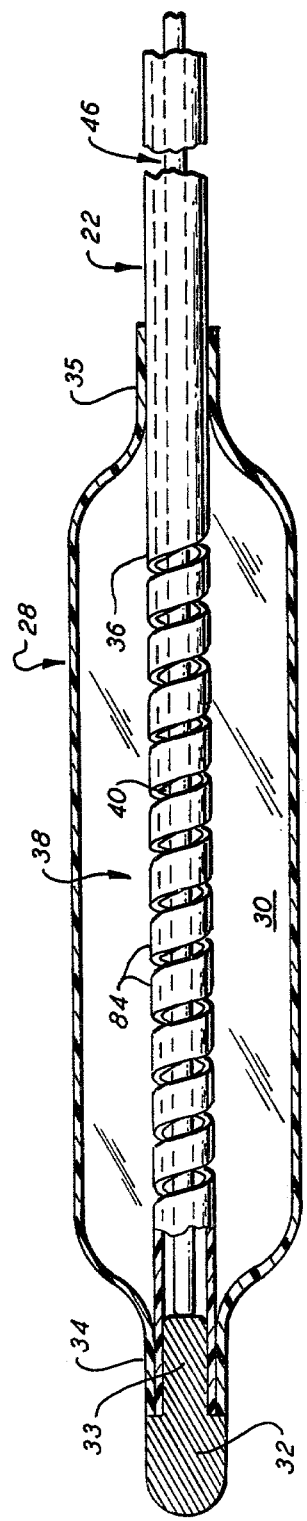
FIG. 7 is a longitudinal section view similar to that of FIG. 1 showing part of a catheter according to still another embodiment of the invention in which the continuously extending opening extends substantially from the proximal end to the distal end of the balloon.

Opening 38 in tube section 36 may be located near the distal end 34 of the balloon as shown in FIG. 1, or the opening may be located near the proximal end 35 of the balloon as shown in FIG. 6. The opening may also be located at the middle of tube section 36 as shown in FIG. 7. Catheters according to the invention may have openings which extend for different lengths of tube section 36, are of different width as described hereinbefore, or the number and size of the helical coils 84 defining the opening may be different. For example, FIG. 1 shows five coils while FIG. 6 shows four, and FIG. 7 shows 11 extending over substantially almost all of the length of tube section 36.

According to the present invention, the propensity for arterial damage and trauma caused by the bulky, stiff prior art catheters having the oblique folds is precluded.

As shown in FIG. 3, the catheter according to the invention is elongated for insertion and female luer 26b is locked to male luer 26a. Thus, the surgeon may use both hands to insert the catheter into the arterial incision. Rod or elongated member 46 may be removed as soon as the balloon is entirely within the blood vessel or the catheter may be advanced further into the vasculature while in itselongated configuration. Upon unlocking the male and female luers, the rod retracts and the balloon assumes its non-elongated, axially-shortened configuration. Indelible marks, 66, 67, 68 (FIG. 1) located at fixed intervals along the catheter may be used to indicate the position of the catheter in the vasculature.

Figure 8:
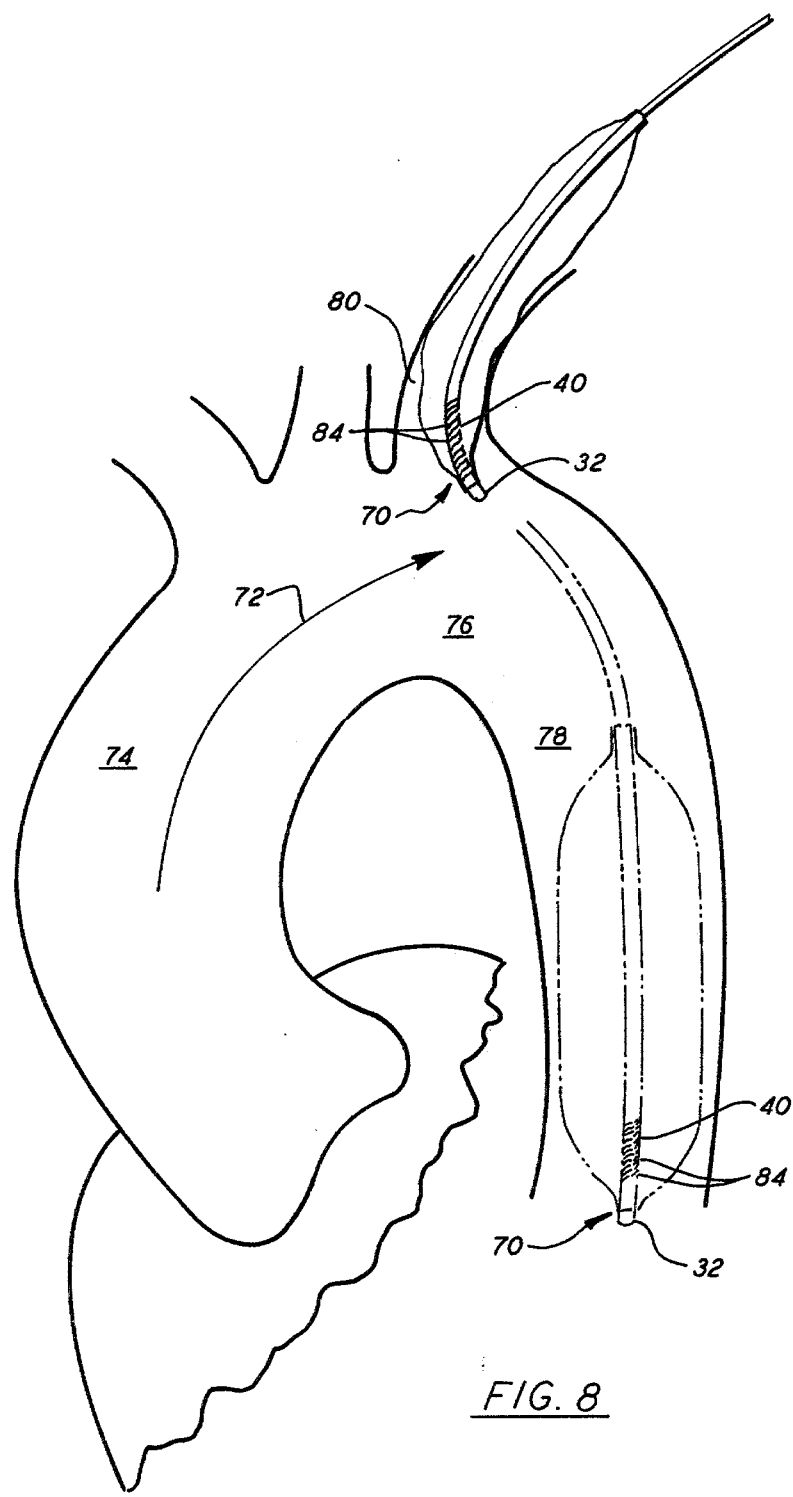
FIG. 8 is a diagramatic illustration showing the catheter of FIG. 1 introduced into the left brachial artery while in the configuration of FIG. 3 (solid lines), and the catheter in the expanded configuration of FIG. 1 (broken lines) in the descending aorta after having been guided from the left brachial artery.

Referring now to FIG. 8, the distal end 70 of the catheter (which includes tip 32 and the helical slit 40) assumes a flacid configuration after the elongating member 46 has been removed. The helical slit 40 and tube 22 are flexible and not resistant to lateral bending. Thus, the catheter, particularly that part within the balloon which includes slit 40, is extremely flexible and is free to follow the curves of the vascular system, the tip 32 guiding the flexible catheter. The natural blood flow, indicated by the arrow referenced 72, in the aorta 74 serves to deflect the nonresistant catheter end 70 into the downstream path of the aortic arch 76 and into the descending aorta 78 where aortic balloon pumping is normally carried out. The catheter is illustrated in solid lines in FIG. 8 entering the aortic arch via the branchial artery 80, and the catheter is shown in phantom in the descending aorta 78 operatively positioned for intra-aortic balloon pumping. A preformed wire of fine diameter may be inserted into the catheter to serve as a "teaching wire" to steer the flexible catheter end 70 into any desired direction. The flexible catheter may also be "flow-directed", i.e., the catheter may be forced through the blood vessel under urging of the blood flow.

Fluid for inflating and deflating the balloon of prior art catheters generally enters and leaves the balloon via ports 82 as shown in FIG. 9. The number, configuration, size and location of the openings must be considered since a rapid, non-turbulent and nonrestrictive flow of fluid into and out of the balloon is desired. Usually in such prior art catheters three or four holes are provided proximate the distal end of catheter having a total communication port area equal to at least about 1½ times the area of the balloon cross-section. Even where a multitude of discrete openings are used, it is difficult to achieve non-turbulent fluid flow.

According to the present invention, helical slit 40 allows rapid, uniform entry and withdrawal of inflating fluid to and from the balloon without adversely affecting the ability of the catheter tube to support the balloon, and, as shown in FIG. 1, the slit occupies five circumferential turns having a normal slit width of about 1/16 inch. This provides a continuous opening having an area of at least ten times the cross-sectional area of the gas supply tube and permits the use of a catheter tube 22 of smaller diameter than one having the discrete openings of the prior art.

In FIG. 10 is shown the balloon portion of another embodiment of a catheter 90 according to the invention in which helical spring 92 is enclosed by balloon 28. The helical spring takes the place of tube section 36 and helical slit 40. Continuously extending opening 38 is formed by the spaces between the coils of the spring and elongation of balloon 28 is accomplished by axially stretching the spring. Catheter 90 includes tip 94 having reduced diameter section 96. Enclosing and affixed to the reduced diameter section 96 of the tip by, for example, electrical resistance welding, adhesive bonding, etc., is one end of a stainless steel sleeve 98. The spring 92 extends about the other end of sleeve 98 and is also affixed to the sleeve by welding or adhesive bonding, for example. Surrounding the stainless steel sleeve 98 between the shoulder 100 of tip 94 and the spring 92 is another flexible sleeve 102 made of polyurethane, for example. Both sleeves 98 and 102 abut shoulder 100. Spring end 104 abuts and bears against sleeve 102 which with sleeve 98 forms a seat for the spring end 104. Balloon end 34 is secured to the tip and to sleeve 102 in a fluid-tight manner as described for catheter 20. At the other end 35 of the balloon, spring 92 extends about one end of another sleeve 106 made of stainless steel, for example, and is affixed thereto as described for sleeve 98 and the spring. Tube 22 encloses the other end of sleeve 106 with the end 108 of the spring bearing against the end 110 of tube 22, i.e. the end 110 with sleeve 106 forms a seat for the spring end 108. The tube 22 is affixed to sleeve 106 in a fluid-tight manner and balloon end 35 is affixed to tube 22 in a fluid-tight manner, as described for catheter 20. Rod 46 is disposed within tube 22 and also within spring 92 and connected to a luer as described for catheter 20. Movement of rod 46 to the left bears against tip section 96 to elongate the balloon as described for catheter 20. Sleeve 98 forms an enclosure for the rod to contain it in the event it is inadvertently slipped through the spaces between the coils of the spring during elongation. The coils of spring 92 may contact each other at points or the spring may be provided with spaced coils and the spacing may vary depending upon the stiffness of the spring and the flexibility desired. Even when the coils of the spring contact each other, fluid will pass between the coils as they are not tightly wound. Additionally, transmural ports 111 may be provided in sleeve 106 in addition to fluid passages between coils of the spring for admitting and withdrawing inflating fluid to and from the balloon. With the spring 92 extending about sleeves 98 and 106 and bearing against sleeve 102 at one end and tube 22 at the other end, the diameter of the supporting means within the balloon is no larger than the diameter of catheter tube 22, as per the embodiments of FIGS. 1-4.

Catheters may be made having helical slits of varying width and having springs with the coils thereof separated by varying spaces according to the invention by first forming the seal between balloon end 34 and tube 22, then elongating slit 40 of tube 22 or spring 92 until the desired width 38 of helical slit 40 or spacing 38 of coils is obtained, and then forming the seal between balloon end 35 and tube 22. The slit or spring is not elongated to its fullest extent and sufficient reserve is left to further elongate the slit or spring upon elongation of the balloon as described hereinbefore. In accordance with the invention, the width 38 of slit 40 and the spacing 38 of the spring coils can not be reduced during pumping to be smaller than the width imparted to the slit and the spacing to the coils during fabrication.

The present invention may be embodied in dual or multi-chamber balloon catheters in addition to the single chamber balloon catheters described hereinbefore. Referring to FIG. 11, dual chamber catheter 110 includes a second or occluding balloon 112 in addition to the pumping balloon 114 similar to balloon 28 of FIG. 1. Occluding balloon 112 is bonded to tube 22 at balloon ends 116, 117 as described for balloon 28. A continuously extending opening 120 in the form of a slit 40 is provided in tube section 122 as described for the opening in FIGS. 1, 6 and 7. Opening 120 is shown to extend for almost all of the length of section 122, similar to the opening in FIG. 7. Preferably the opening 120 into balloon 112 is greater than the area formed by the opening 124 also formed by a slit 40 into balloon 114 to insure that the occluding balloon 112 inflates before displacement of pumping balloons 114, thereby insuring optimal unidirectional balloon pumping action in the direction of the heart 126 and the aortic arch 76 as shown in FIG. 12.

It is understood that the position of the occluding balloon 112 may be other than between balloon 114 and luer 26. In some instances, unidirectional pumping is more efficacious if the occluding balloon 112 is placed between tip 32 and balloon 114. Such a catheter 128 is shown in FIG. 13 and provides optimal unidirectional pumping action in the direction of the heart 126 and aortic arch 76. Balloons 112 and 114 of FIGS. 11-13 may be separate or, as shown, they may comprise a single balloon which forms separate balloon chambers when secured to tube 22 intermediate the ends of the single balloon.

In FIG. 14 is shown another embodiment of a dual chamber catheter 130. Catheter 130 includes an occluding balloon 112 and a pumping balloon 114 similar to catheter 110 of FIG. 11. Catheter 130 also includes a helical spring 92 and a tip arrangement at the distal end of the pumping chamber and an arrangement at the proximal end of the occluding chamber similar to those described for catheter 90 in FIG. 10. The spring 92 in the neck region 132 is enclosed in a heat shrunk Teflon sleeve 134 to protect the balloon neck from damage under action of the spring such as pinching. The thickness of sleeve 134 does not exceed the thickness of tube 22 so that the diameter of the support in the neck is not larger than the diameter of the tube, as is the case for the entire catheter 130.

The advantages of the present invention, as well as certain changes and modifications of the disclosed embodiments thereof, will be readily apparent to those skilled in the art. It is the applicant's intention to cover by his claims all those changes and modifications which could be made to the embodiments of the invention herein chosen for the purpose of the disclosure without departing from the spirit and scope of the invention. Protection by Letters Patent of this invention in all its aspects as the same are set forth in the appended claims is sought to the broadest extent that the prior art allows.

We claim:

1. A catheter comprising an inflatable and deflatable chamber having a proximal end and a distal end, said chamber in use being adapted to have substantially the same surface area when inflated and when deflated, a catheter tube portion having a passage communicating with the interior of said chamber for admitting fluid into and withdrawing fluid from said chamber, means extending in said chamber substantially to said distal end of said chamber for supporting said chamber, said supporting means, said catheter tube portion, and said chamber being connected substantially at said proximal end of said chamber, said supporting means and said chamber being connected substantially at said distal end of said chamber, said chamber being sealed substantially at said proximal and distal ends thereof, said supporting means within said chamber having at least one space therein which at least partially extends transversely of said supporting means and means for selectively increasing said space substantially axially of said supporting means to thereby elongate said supporting means sufficiently to elongate said chamber and transversely decrease the size of said chamber, whereby insertion of said catheter into a body passageway or the like is substantially aided.

2. The catheter recited in claim 1, wherein said supporting means includes a member secured to said catheter tube portion, said member having a passage therein communicating with said catheter tube portion passage, said space comprising a continuously extending opening in communication with said passage in said member in a portion of said member enclosed within said chamber for admitting fluid to and withdrawing fluid from said chamber, the area of said opening and the cross-sectional area of said passage in said member each being substantially at least equal to the cross-sectional area of said catheter tube portion passage.

3. The catheter recited in claim 2, wherein the area of said opening is substantially greater than the cross-sectional area of said catheter tube portion passage.

4. The catheter recited in claim 2, wherein said opening is a helical slit extending along said portion of said member.

5. The catheter recited in claim 2, wherein said member forms part of said catheter tube portion.

6. The catheter recited in claim 1, wherein said supporting means comprises a helical spring connected to said catheter tube portion, a space between coils of said spring defining said space at least partially extending transversely of said supporting means.

7. The catheter recited in claim 6, wherein said supporting means further includes a sleeve for connecting said spring to said catheter tube portion.

8. The catheter recited in claim 1, wherein said increasing means comprises a rod extending, and being operative to be axially moved, within said supporting means against the end of said catheter adjacent the distal end of said chamber to increase said space axially of said supporting means and thereby elongate said chamber and said supporting means.

9. The catheter recited in claim 8, wherein said supporting means comprises a hollow tubular member in which is disposed said rod, said space comprising a helical slit in said tubular member in communication with said catheter tube portion passageway for admitting fluid to and withdrawing fluid from said chamber, said supporting means being elongated by widening said slit upon axial movement of said rod against said catheter end.

10. The catheter recited in claim 8, wherein said supporting means comprises a hollow tubular member secured to said catheter tube portion in which is disposed said rod and a helical spring secured at one end thereof to said tubular member and enclosed by said chamber, said helical spring being connected at the other end thereof to said catheter end, said space comprising a helical space extending between coils of said spring in communication with said catheter tube portion passage for admitting fluid to and withdrawing fluid from said chamber, said supporting means being elongated by elongation of said spring and widening of said space upon axial movement of said rod against said catheter end.

11. The catheter recited in claim 1, wherein said supporting means includes a hollow tubular member secured to said catheter tube portion and further comprising a rigid tip secured to the end of said tubular member adjacent said chamber distal end and forming the catheter distal end.

12. The catheter recited in claim 1 and further comprising means for venting the interior of said chamber.

13. A catheter comprising an inflatable and deflatable chamber having a proximal end and a distal end, said chamber in use being adapted to have substantially the same surface area when inflated and when deflated, a catheter tube portion having a passage for admitting fluid to and withdrawing fluid from said chamber, a first member extending in said chamber substantially to said distal end of said chamber for supporting said chamber, said first member, said catheter tube portion and said chamber being connected substantially at said proximal end of said chamber, said chamber and said first member being connected substantially at said distal end of said chamber, said chamber being sealed substantially at said proximal and distal ends thereof, said first member having a passage therein in communication with said catheter tube portion passage and an opening within said chamber in communication with said passage in said first member and with said chamber for admitting fluid to and withdrawing fluid from said chamber, said opening of at least partially extending transversely of said first member, an elongated member extending in said catheter tube portion and in said first member and having an end which bears against the end of said catheter at or adjacent to said distal end of said chamber for increasing said opening substantially axially of said first member and thereby axially elongating said first member and said chamber to transversely decrease the size of said chamber upon axial movement of said elongated member against said catheter end.

14. The catheter recited in claim 13, wherein said first member is a hollow tubular member and said opening therein is a slit, the width of said slit being increased upon movement of said elongated member to elongate said hollow member and said chamber.

15. The catheter recited in claim 13, wherein said first member is hollow and includes an opening in the form of a helically-extending slit, said slit increasing in width upon movement of said elongated member to elongate said hollow member and said chamber.

16. The catheter recited in claim 13, wherein said first member includes a helical spring connected to said distal end of said chamber and to said catheter tube portion, said opening being a helically extending space between coils of the spring.

17. The catheter recited in claim 13, 15 or 16 wherein said elongated member is rod-like.

18. The catheter recited in claim 13, wherein said first member forms part of said catheter tube portion.

* * * * *

UNITED STATES PATENT AND TRADEMARK OFFICE
CERTIFICATE OF CORRECTION

PATENT NO. : 4,276,874

DATED : July 7, 1981

INVENTOR(S) : Wolvek, et al.

It is certified that error appears in the above—identified patent and that said Letters Patent is hereby corrected as shown below:

In the Abstract, line 9, change "chanber" to --chamber--.

Column 3, line 55, change "inention" to --invention--.

Column 4, line 22, change "becaue" to --because--.

Column 5, line 41, change "longitudinally" to --longitudinal--.

Column 8, line 15, change "itselongated" to --its elongated--;

line 36, change "branchial" to --brachial--.

Column 11, line 55, change "passageway" to --passage--.

UNITED STATES PATENT AND TRADEMARK OFFICE
CERTIFICATE OF CORRECTION

PATENT NO. : 4,276,874

DATED : July 7, 1981

INVENTOR(S) : Wolvek, et al.

It is certified that error appears in the above—identified patent and that said Letters Patent is hereby corrected as shown below:

Column 12, line 36, omit "of" (first occurrence).

*Signed and Sealed this*

*Fifteenth* Day of *December 1981*

[SEAL]

Attest:

Attesting Officer

GERALD J. MOSSINGHOFF

*Commissioner of Patents and Trademarks*